United States Patent
Kim et al.

(10) Patent No.: US 10,975,130 B2
(45) Date of Patent: Apr. 13, 2021

(54) COMPOSITION FOR PREVENTING HAIR LOSS OR PROMOTING HAIR GROWTH

(71) Applicant: BR PHARM CO., LTD., Wonju-si (KR)

(72) Inventors: Seok Soon Kim, Wonju-si (KR); Boon Saeng Park, Seoul (KR); Il Gi Kim, Samcheok-si (KR)

(73) Assignee: BR PHARM CO., LTD., Wonju-si (KR)

( * ) Notice: Subject to any disclaimer, the term of this patent is extended or adjusted under 35 U.S.C. 154(b) by 0 days.

(21) Appl. No.: 16/676,393

(22) Filed: Nov. 6, 2019

(65) Prior Publication Data

US 2020/0317741 A1    Oct. 8, 2020

(30) Foreign Application Priority Data

Apr. 4, 2019   (KR) .................. 10-2019-0039708

(51) Int. Cl.
*A61K 38/00* (2006.01)
*A61P 17/14* (2006.01)
*C07K 14/47* (2006.01)

(52) U.S. Cl.
CPC .......... *C07K 14/4705* (2013.01); *A61P 17/14* (2018.01); *A61K 38/00* (2013.01)

(58) Field of Classification Search
CPC ..... A61K 38/00; A61P 17/14; C07K 14/4705; C07K 14/47
USPC ....................................................... 514/20.7
See application file for complete search history.

(56) References Cited

U.S. PATENT DOCUMENTS 6,485,972 B1 * 11/2002 McMahon ........... A61K 38/177 435/374
9,168,300 B2 * 10/2015 Gurney .................. C07K 14/71

FOREIGN PATENT DOCUMENTS

EP          3121196 A1 *  1/2017  .............. A61P 17/16

OTHER PUBLICATIONS

Alopecia from Merck Manual, pp. 1-9. Accessed Nov. 2, 2020. (Year: 2020).*
Alopecia Areata from Merck Manual, pp. 1-3. Accessed Nov. 2, 2020. (Year: 2020).*
Lee et al, "Therapeutic efficacy of autologous platelet-rich plasma and polydeoxyribonucleotide on female pattern hair loss," Wound Repair and Regeneration, 2015, 23: 30-36. (Year: 2015).*

* cited by examiner

*Primary Examiner* — Julie Ha
(74) *Attorney, Agent, or Firm* — Revolution IP, PLLC

(57) ABSTRACT

A composition for preventing the hair loss or promoting the hair growth includes Wnt protein-derived peptides and polydeoxyribonucleotides as an active ingredient, and increases the secretion of β-catenin. By the cell activation and activation of signal transduction pathway for promoting the hair growth signaling system, the growth of hair constituent cells, such as keratinocytes, fibroblasts and dermal papilla cells, is increased to prevent the hair loss or promote the hair growth. Wnt protein-derived peptides and polydeoxyribonucleotides are used as a cosmetic composition, a pharmaceutical composition or a health food composition for preventing the hair loss or promoting the hair growth.

9 Claims, 8 Drawing Sheets

Specification includes a Sequence Listing.

A

B

C

COMPOSITION FOR PREVENTING HAIR LOSS OR PROMOTING HAIR GROWTH

CROSS-REFERENCE TO RELATED APPLICATION

This application claims priority to and the benefit of Korean Patent Application No. 10-2019-0039708 filed in the Korean Intellectual Property Office on 04, 04, 2019, the entire contents of which are incorporated herein by reference.

BACKGROUND OF THE DISCLOSURE

1. Field of the Disclosure

The present invention relates to a composition for preventing hair loss or promoting hair growth comprising a novel Wnt protein-derived peptide, polydeoxyribonucleotide or a mixture thereof as an active ingredient.

2. Description of the Related Art

Hair is a solid cone fiber composed of tightly adhered and keratinized epithelial cells and about 100,000 to 150,000 hairs are formed in the hair follicles of the scalp, and it has been known that the number of hair follicles is determined at birth and is not generated further after birth. Each hair represents a different cycle: an anagen in which hair grows, a catagen in which its growth stops and the hair bulb shrinks, and a telogen in which the dermal papilla starts to act or develop new hair, thereby resulting in the loss of old hair and the hair grows and falls off by repeating this cycle. This cycle is repeated over three to six years, ranging from 3-5 years for men and 4-6 years for women. Normally, it is known that 50-70 hairs are fallen off on daily average, and hair at the anagen, catagen and telogen account for about 88%, 1% and 11% of the total hair, respectively.

Alopecia refers to a symptom in which hairs of at least 100 hairs are dropped out per day, hair at the anagen is decreased, and hairs at the catagen and the telogen are increased. As the hair loss progresses, the hair rate of the telogen is rapidly increased and the hair rate of the anagen is decreased, accordingly. Hair loss may generally include hereditary androgenetic alopecia (baldness), alopecia areata, tinea capitis due to fungal infections, telogen alopecia, trichoti lomania, hair growth disorders and the like. The most common hair loss includes baldness (male-pattern alopecia), female-pattern alopecia, alopecia areata, and telogen effluvium, etc.

The causes of hair loss are various. Genetic factors and male hormone, androgen are considered important factors for baldness, and some female-pattern alopecia are estimated to be caused in the same route as male-pattern alopecia, but there are differences of clinical pattern. Alopecia areata is thought to be caused by autoimmune diseases. Telogen alopecia is a temporary hair loss that occurs after severe physical and mental stress, such as endocrine diseases, nutritional deficiencies, drugs, childbirth, fever and surgery and it occurs by being fallen off due to transition to telogen of the part of the hair which does not go through the growth period Currently, there are only two FDA-approved hair loss treatment products: Finasteride and Minoxidil. Finasteride, which is male-pattern alopecia remedy, inhibits hair loss by using a mechanism of inhibiting 5α-reductase, an enzyme that converts male hormones into dihydrotestosterone (DHT), a hair loss-inducing factor, as a male hair loss treatment agent. Minoxidil inhibits hair loss by increasing blood flow to the scalp. However, these therapies constantly are reported to have some side effects, and also, their treatment effect is temporary and limited. Hair loss is caused by a combination of factors, not any one cause and the resolution of some causes cannot completely cure it.

Accordingly, various researches on hair loss have been conducted in western medicine and oriental medicine, and various treatment methods have been tried. Researches on natural products, steroids, autoimmune suppression, etc. are being conducted, and treatments using laser therapy, autologous platelet-rich plasma application, derma roller or stem cells, etc. have been performed. However, these treatments also do not approach complexly to solve the causes of various hair loss, and scientifically untested medical procedures have a disadvantage in that they are ineffective compared to price. Therefore, there is an urgent need to develop new medication for hair loss which is scientifically proven and more economical in terms of cost.

SUMMARY OF THE DISCLOSURE

An object of the present invention is to provide a peptide for preventing the hair loss or promoting the hair growth.

Another object of the present invention is to provide a cosmetic composition for preventing the hair loss or promoting the hair growth.

The third object of the present invention is to provide a pharmaceutical composition for preventing the hair loss or promoting the hair growth.

The fourth object of the present invention to provide a health food composition for preventing the hair loss or promoting the hair growth.

In order to achieve the above object, the present invention provides a peptide comprising at least any one of the amino acid sequence selected from the group consisting of SEQ ID NO: 1 and SEQ ID NO: 2.

Also, the present invention also provides a cosmetic composition for preventing hair loss or promoting hair growth comprising a peptide comprising at least any one of the amino acid sequence selected from the group consisting of SEQ ID NO: 1 and SEQ ID NO: 2, polydeoxyribonucleotide or a mixture thereof, as an active ingredient.

In addition, the present invention also provides a pharmaceutical composition for preventing hair loss or promoting hair growth comprising a peptide comprising at least any one of the amino acid sequence selected from the group consisting of SEQ ID NO: 1 and SEQ ID NO: 2, polydeoxyribonucleotide or a mixture thereof, as an active ingredient.

Furthermore, the present invention provides a health food composition for preventing hair loss or promoting hair growth comprising a peptide comprising at least any one of the amino acid sequence selected from the group consisting of SEQ ID NO: 1 and SEQ ID NO: 2, polydeoxyribonucleotide or a mixture thereof, as an active ingredient.

DETAILED DESCRIPTION OF THE EMBODIMENTS

Figure 1:
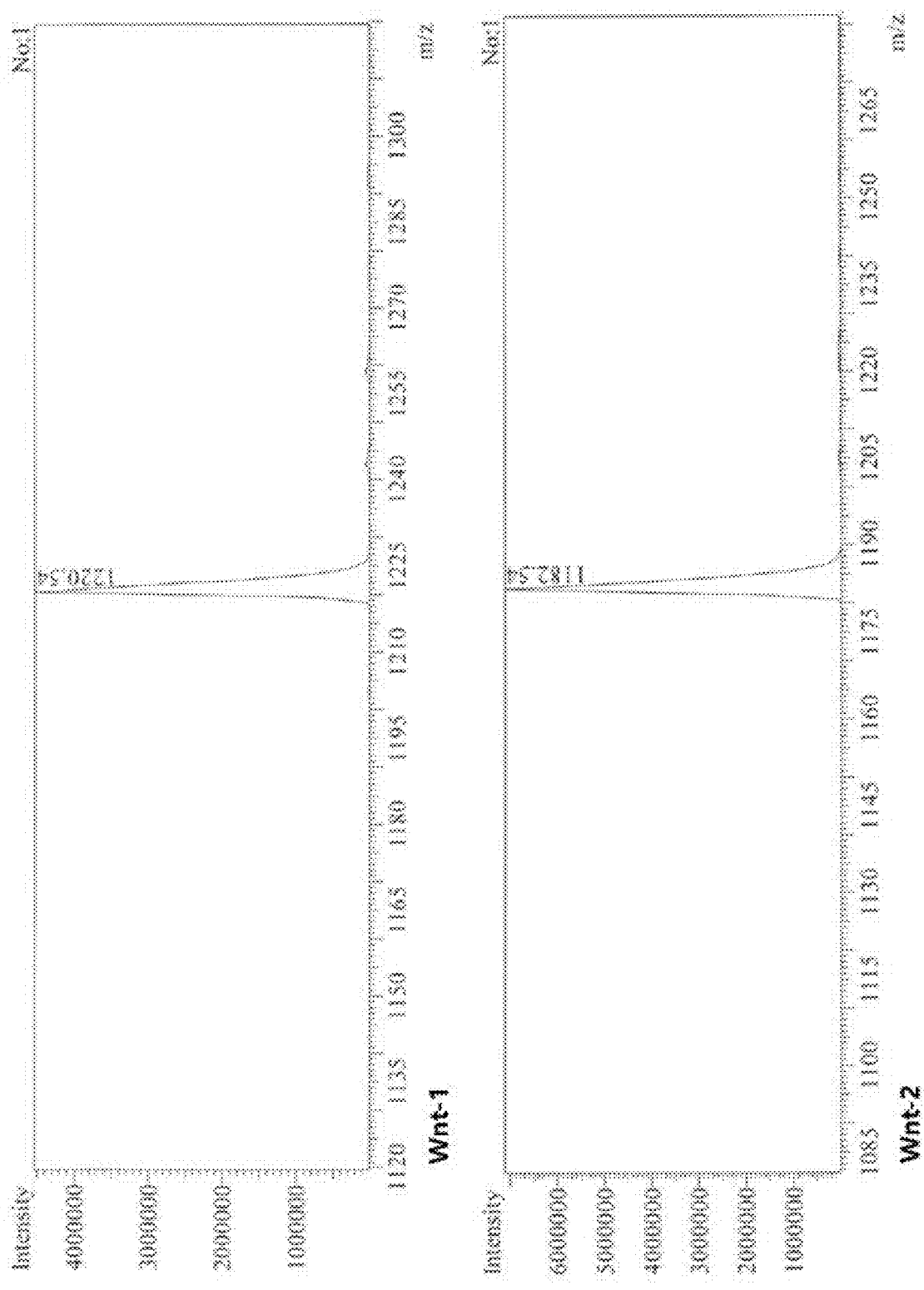
FIG. 1 shows the results of high performance liquid chromatography analysis of novel peptide-1 (Wnt-1, SEQ ID NO: 1) and peptide-2 (Wnt-2, SEQ ID NO: 2), which are derived from Wnt protein.

The inventors of the present invention confirmed that novel Wnt proteins-derived peptides (Wnt-1 or/and Wnt-2), polydeoxyribonucleotides or mixtures thereof activate the Wnt signaling system to increase the secretion and activity of β-catenin and to promote the growth of keratinocytes, fibroblasts and dermal papilla cells, which are important for hair root generation, and to induce hair differentiation at the anagen, and completed the present invention.

Accordingly, the present invention provides a peptide comprising at least any one of the amino acid sequence selected from the group consisting of SEQ ID NO: 1 and SEQ ID NO: 2.

The peptide may be acetylated at the N-terminus of the amino acid sequence.

The peptide may be a peptide derived from Wnt protein. The Wnt protein-derived peptide is a peptide that performs a function similar to that of a natural Wnt protein and binds to a receptor to perform a function such as that of a growth factor.

The peptide may prevent the hair loss and promote the hair growth.

The present invention also provides a cosmetic composition for preventing hair loss or promoting hair growth comprising a peptide comprising at least any one of the amino acid sequence selected from the group consisting of SEQ ID NO: 1 and SEQ ID NO: 2, polydeoxyribonucleotide or a mixture thereof, as an active ingredient.

The peptide may be acetylated at the N-terminus of the amino acid sequence.

The peptide may be a peptide derived from Wnt protein. The Wnt protein-derived peptide is a peptide that performs a function similar to that of a natural Wnt protein and binds to a receptor to perform a function such as that of a growth factor.

The polydeoxyribonucleotide is separated from the testis of fish and the fish may be selected from the group consisting of salmon, trout, herring, pollock and cod, but it is not limited thereto.

The polydeoxyribonucleotide may have a number average molecular weight of 350 to 2000 kDa.

In addition, the composition increases the secretion of β-catenin to promote the growth of keratinocytes, fibroblasts and dermal papilla cells, and increases the expression of c-myc, thereby preventing the hair loss and promoting the hair growth.

The composition may be formulated in a formulation selected from the group consisting of hair tonic, hair conditioner, hair essence, hair lotion, hair nutrition lotion, hair shampoo, hair rinse, hair treatment, hair cream, hair nourishing cream, hair moisturizer cream, hair massage cream, hair wax, hair aerosol, hair pack, hair nutrition pack, hair soap, hair cleansing foam, hair oil, hair drying agent, hair preservative, hair dye, hair wave agent, hair bleach, hair gel, hair glaze, hair dressinger, hair lacquer, hair moisturizer, hair mousse and hair spray, but it is not limited thereto.

When the composition of the present invention is a cosmetic composition, the cosmetic composition may include, in addition to the active ingredient, conventional auxiliaries such as stabilizers, solubilizers, vitamins, pigments and flavors, and carriers. In addition, the cosmetic composition may further include a skin absorption enhancer to enhance the effect.

When the composition of the present invention is a cosmetic composition, the formulation of the cosmetic composition may be prepared in any formulation commonly prepared in the art, for example, the cosmetic composition may be face lotion, emulsion, skin lotion, toner, lotion, essence, sunscreen, cream, makeup base, foundation, powder, pack, gel, ointment, patch, stick, shampoo, rinse, spray, makeup remover and cleanser, etc., but it is not limited thereto.

When the formulation is paste, cream or gel, it may use animal oil, vegetable oil, wax, paraffin, starch, tragacanth, cellulose derivative, polyethylene glycol, silicone, bentonite, silica, talc or zinc oxide and the like, as the carrier component.

When the formulation is powder or spray, it may use lactose, talc, silica, aluminum hydroxide, calcium silicate or polyamide powder, as the carrier component, and in particular, the spray may additionally include a propellant such as chlorofluorohydrocarbon, propane/butane or dimethyl ether.

When the formulation is solution or emulsion, solvent, solubilizer or emulsifying agent are used as the carrier component, for examples water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid esters of sorbitan.

When the formulation is suspension, it may use liquid diluents such as water, ethanol or propylene glycol, suspending agents such as ethoxylated isostearyl alcohol, polyoxyethylene sorbitol esters, and polyoxyethylene sorbitan esters, microcrystalline cellulose, aluminum metahydroxide, bentonite, agar or tragacanth, as the carrier component.

The present invention also provides a pharmaceutical composition for preventing hair loss or promoting hair growth comprising a peptide comprising at least any one of the amino acid sequence selected from the group consisting of SEQ ID NO: 1 and SEQ ID NO: 2, polydeoxyribonucleotide or a mixture thereof, as an active ingredient.

The peptide may be acetylated at the N-terminus of the amino acid sequence.

When the composition according to the present invention is a pharmaceutical composition, for administration, it may include a pharmaceutically acceptable carrier, excipient or diluent in addition to the active ingredient described above. The carrier, excipient and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil.

The pharmaceutical compositions according to the present invention may be formulated in the form of oral formulations such as powders, granules, tablets, capsules, suspensions, emulsions, syrups or aerosols, external preparations, suppositories or sterile injectable solutions according to respective conventional methods. In detail, when formulated, it may be prepared by using diluents or excipients such as fillers, bulking agents, binders, wetting agents, disintegrating agents, and surfactants which are commonly used. Solid preparations for oral administration include tablets, pills, powders, granules, capsules and the like, but they are not limited thereto. Such solid preparations may be prepared by mixing at least one excipient such as starch, calcium carbonate, sucrose, lactose, gelatin, etc. in addition to the active ingredient. In addition to simple excipients, lubricants such as magnesium stearate, talc may also be used. It may be prepared by adding various excipients such as humectants, sweeteners, fragrances, preservatives and the like in addition to liquids or liquid paraffin for oral use. Formulations for parenteral administration include sterile aqueous solutions, non-aqueous solvents, suspensions, emulsions, freeze drying agents. As the non-aqueous solvents and suspensions, propylene glycol, polyethylene glycol, vegetable oils such as olive oil, injectable esters such as ethyl oleate, and the like may be used. As the base of the suppository, witepsol, macrogol, tween 61, cacao butter, laurinum, glycerogelatin and the like may be used.

Suitable dosages of the pharmaceutical compositions of the present invention vary according to the condition and weight of the patient, the severity of the disease, the form of the drug, and the time, but can be appropriately selected by those skilled in the art, and therefore the daily dosage of the composition is preferably 0.001 mg/kg to 50 mg/kg and it can be administered once or divided into several times as needed.

The present invention provides a health food composition for preventing hair loss or promoting hair growth comprising a peptide comprising at least any one of the amino acid sequence selected from the group consisting of SEQ ID NO: 1 and SEQ ID NO: 2, polydeoxyribonucleotide or a mixture thereof, as an active ingredient.

The peptide may be acetylated at the N-terminus of the amino acid sequence.

When the composition according to the present invention is a health food composition, it may include various nutrients, vitamins, minerals (electrolytes), flavors such as synthetic flavors and natural flavors, etc., colorants and fillers (cheese, chocolate, etc.), pectic acid and its salts, alginic acid and its salts, organic acids, protective colloid thickeners, pH adjusting agents, stabilizers, preservatives, glycerin, alcohols, carbonating agents used in carbonated drinks, and the like. Besides, it may contain flesh for the preparation of natural fruit juices, synthetic fruit juices and vegetable drinks. These components may be used independently or in combination. In addition, the health functional food composition may be in the form of any one of meat, sausage, bread, chocolate, candy, snack, confectionery, pizza, ramen, gum, ice cream, soup, beverage, tea, functional water, drink, alcohol and vitamin complex.

In addition, the health functional food composition may further include a food additive and it suitability as a food additive is determined by the standards for the applicable item in accordance with General Regulations and General Test Methods of Korean Food Additives Codex approved by the Ministry of Food and Drug Safety, unless otherwise provided.

Examples of the items published in the above-mentioned Korean Food Additives Codex include chemical synthetics such as ketones, glycine, potassium citrate, nicotinic acid, and cinnamic acid and the like, natural additives such as persimmon extract, licorice extract, crystalline cellulose, kaoliang color and guar gum and the like, mixed preparations such as L-sodiumglutamate preparation, alkaline agents for noodles, preservative formulation and a tar color formulation and the like.

At this time, the content of the composition according to the present invention added to the food during the production of the health functional food composition can be appropriately increased or decreased as needed.

Hereinafter, examples will be described in detail to help understand the present invention. However, the following examples are merely to illustrate the content of the present invention is not limited to the scope of the present invention. The embodiments of the present invention are provided to more completely explain the present invention to those skilled in the art.

Example 1: Preparation of Novel Peptides Derived from Wnt Protein

In order to produce a novel peptide derived from the Wnt protein of the present invention, the Wnt protein family was examined and the function of each part of the Wnt protein was predicted using the BlastP program. Of these, the potential binding to receptor proteins is explored and the amino acid sequence of the predicted site was optimized to select and construct the peptide of the present invention.

A peptide was synthesized by Peptron. A desired peptide was synthesized by Fmoc solid-phase method in the automatic peptide synthesizer (PeptrEX-R48) and the synthetic peptide was separated from the resin. The peptide was purely separated and analyzed by reverse-phase HPLC (Prominence LC-20AB, Shimadzu, Japan) using Shiseido capcell pak C18 analytical RP column. The peptide is represented by the amino acid sequence of Table 1 below and the N-terminus of the amino acid sequence is acetylated (FIG. 1).

TABLE 1

| | Amino acid sequence |
|---|---|
| Wnt-1 | MCCGRGYDQF |
| Wnt-2 | MCCGRGYNYH |

Example 2: Analysis of Cell Growth by Polydeoxyribonucleotides

Dermal papilla cells (Promocells) were cultured in an incubator at 37° C., 5% $CO_2$ using DMEM medium (Dulbeco's Modified Eagle's Medium) containing 10% fetal bovine serum (FBS) and 1% penicillin/streptomycin.

Cells were recovered by treating the cultured cells with trypsin/EDTA, and then the number of cells was measured using a hemacytometer. The cells were seeded in 96 well plates at $3\times10^3$ cells/200 μL/well and then stabilized for at least 4 hours. Thereafter, the medium was removed, diluted in DEME medium so as to be the polydeoxyribonucleotide (PDRN) of 50, 100, 200 μg/mL concentration and then treated with cells and cultured for 72 hours in an incubator at 37° C., 5% $CO_2$.

Subsequently, the cells were recovered by treating them with trypsin/EDTA and then the number of cells was measured using a hematocytometer. Cell growth rate was analyzed by calculating percentages based on the control group without the treatment with PDRN.

Figure 2:
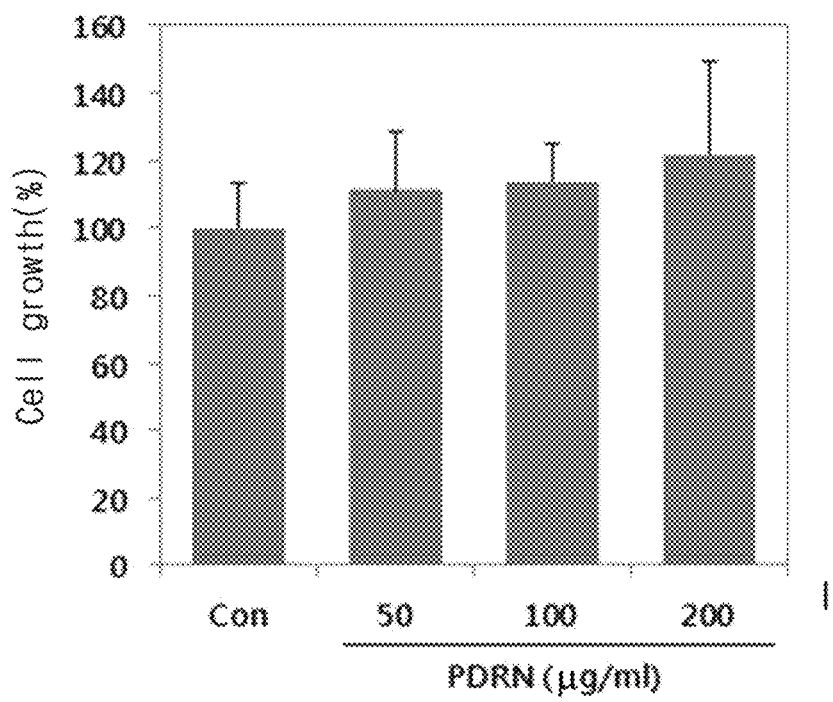
FIG. 2 shows the effect of promoting cell growth by polydeoxyribonucleotide (PDRN) using dermal papilla cells, and microscopic images thereof.
Figure 2:
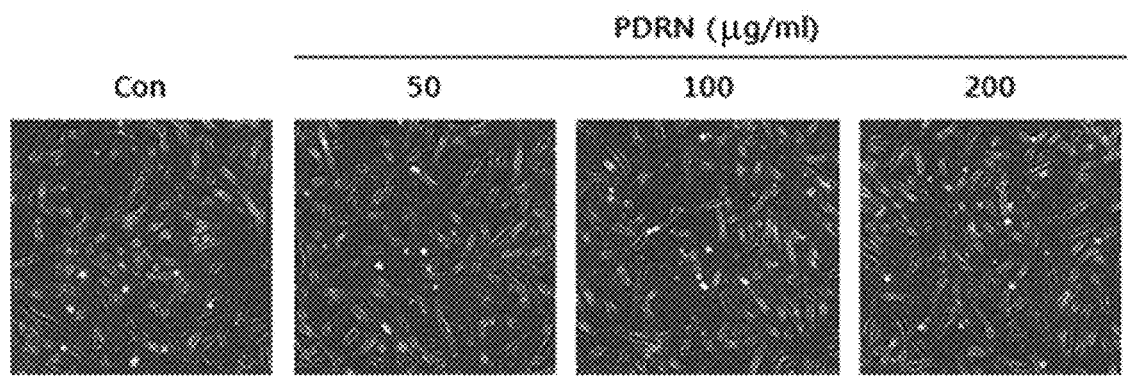

As a result, as shown in FIG. 2, it was confirmed that the growth rate of the dermal papilla cells increases as the PDRN treatment concentration increases.

Example 3: Analysis of Cell Growth by Wnt-Derived Peptides

To confirm the shape change and proliferation rate of cells, keratinocytes T0020001 (AddexBio), fibroblasts (ATCC), and dermal papilla cells were cultured in DMEM medium containing 10% fetal bovine serum and 1% penicillin/streptomycin.

After the cells were recovered by treating the cultured cells with trypsin/EDTA and the number of cells was measured using a hematocytometer. The cells were seeded in 96 well plates at $3\times10^3$ cells/200 μL/well and stabilized for at least 4 hours.

Thereafter, the medium was removed, diluted with DEME medium so as to be the Wnt peptides (Wnt-1, Wnt-2) of 10, 100, 1000, and 10000 ng/mL and then treated with cells and cultured for 72 hours in an incubator at 37° C., 5% $CO_2$. The cells were then observed by a microscope to analyze the morphology and growth rate of the cells.

Figure 3:
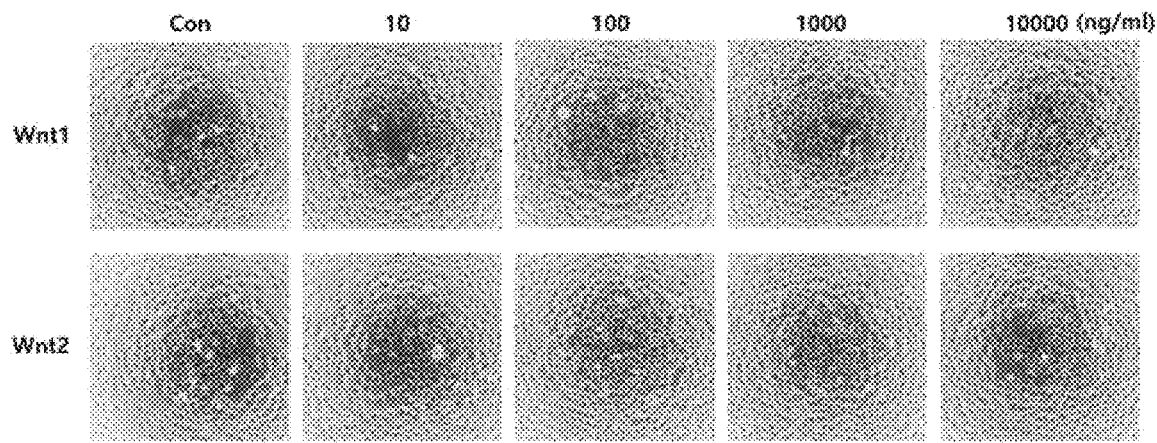
FIG. 3 shows the effect of promoting cell growth by Wnt-1 or Wnt-2 using (A) keratinocytes, (B) fibroblasts and (C) dermal papilla cells, and microscopic images thereof.
Figure 3:
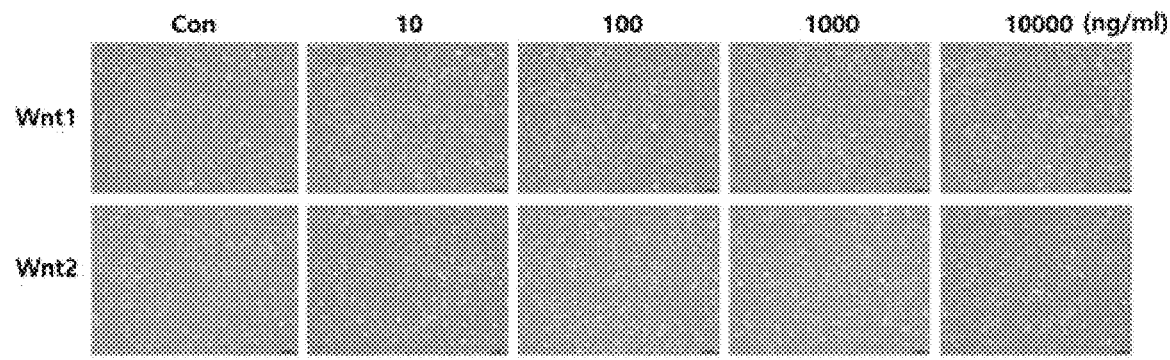
Figure 3:
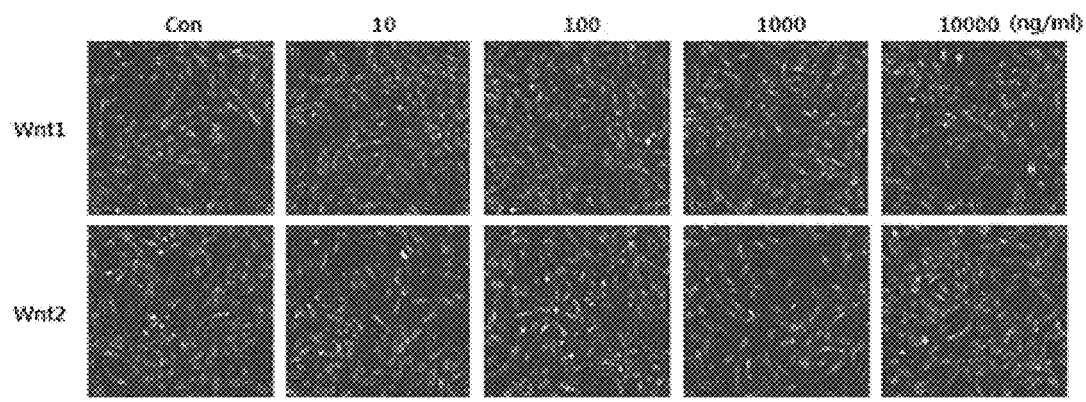
Figure 4:
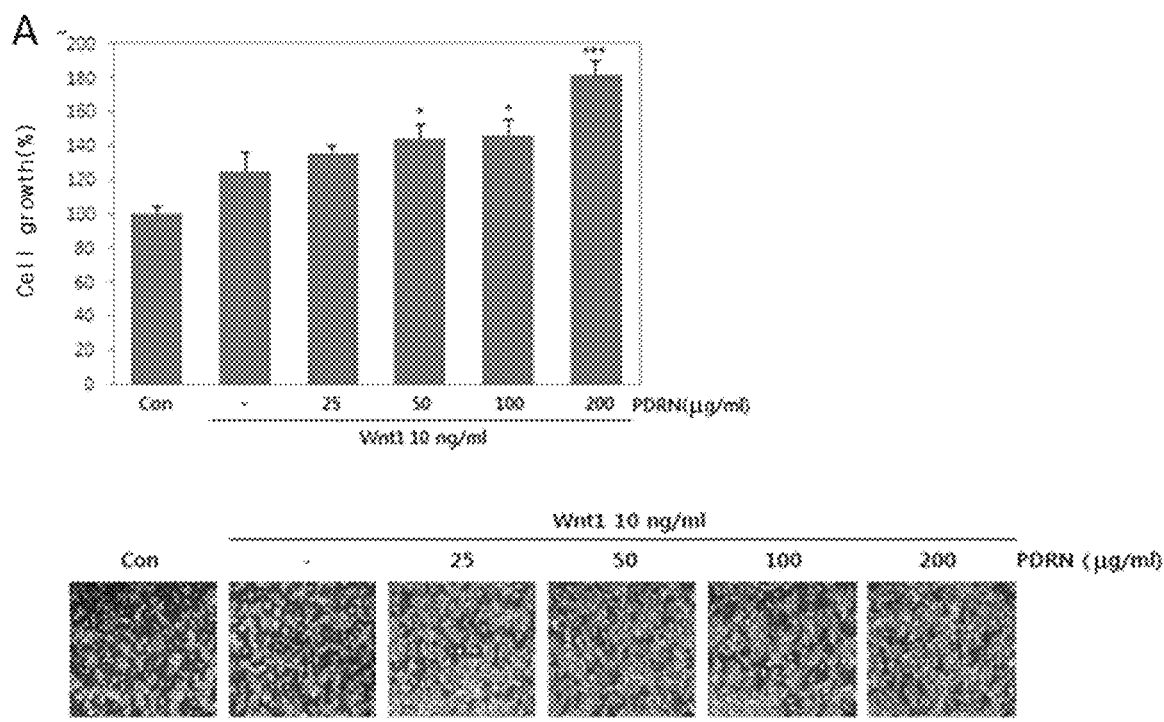
FIG. 4 shows the effect of promoting cell growth by (A) Wnt-1+PDRN or (B) Wnt-2+PDRN using keratinocytes, and microscopic images thereof.
Figure 4:
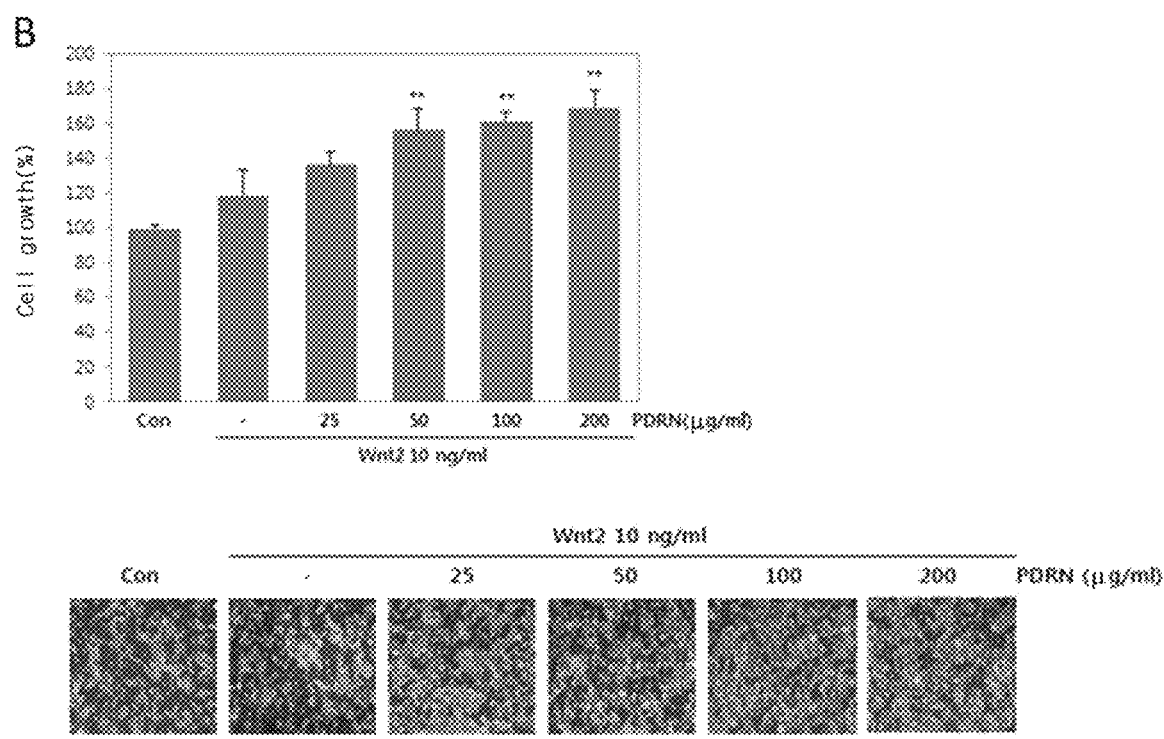

As a result, as shown in FIG. 3, in the keratinocytes as the concentration of the Wnt-1 peptide increased, the growth rate of the cells was increased, and the concentration of 100 ng/mL Wnt-2 peptide showed the highest cell growth rate (FIG. 3A). In addition, fibroblasts exhibited a growth effect at a concentration of 10 ng/mL of the Wnt-1 peptide and similar cell growth rates at high concentrations, whereas no change was observed in the Wnt-2 peptide compared to the control group (FIG. 3B). Finally, in dermal papilla cells, both Wnt-1 peptide and Wnt-2 peptide showed the highest cell growth rate at 100 ng/mL (FIG. 3C).

Example 4: Analysis of Cell Growth by Treatment of Wnt Peptide in Conjunction with PDRN As in Example 1, the dermal papilla cells were seeded in 96 well plates at $3\times10^3$ cells/200 μL/well and stabilized for at least 4 hours. Thereafter, the medium was removed, diluted with DEME medium so as to be polydeoxyribonucleotide (PDRN, BR Pharm Co. Ltd.) of 25, 50, 100 μg/mL and Wnt-1 peptide+Wnt-2 peptide of 0.1 μg/mL (each 0.05 μg/mL) and then treated with cells and cultured for 72 hours in an incubator at 37° C., 5% $CO_2$.

Subsequently, the cells were recovered by treating them with trypsin/EDTA and then the number of cells was measured using a hematocytometer. Cell growth rate was analyzed by calculating percentages based on the control group without the treatment with PDRN.

Figure 5:
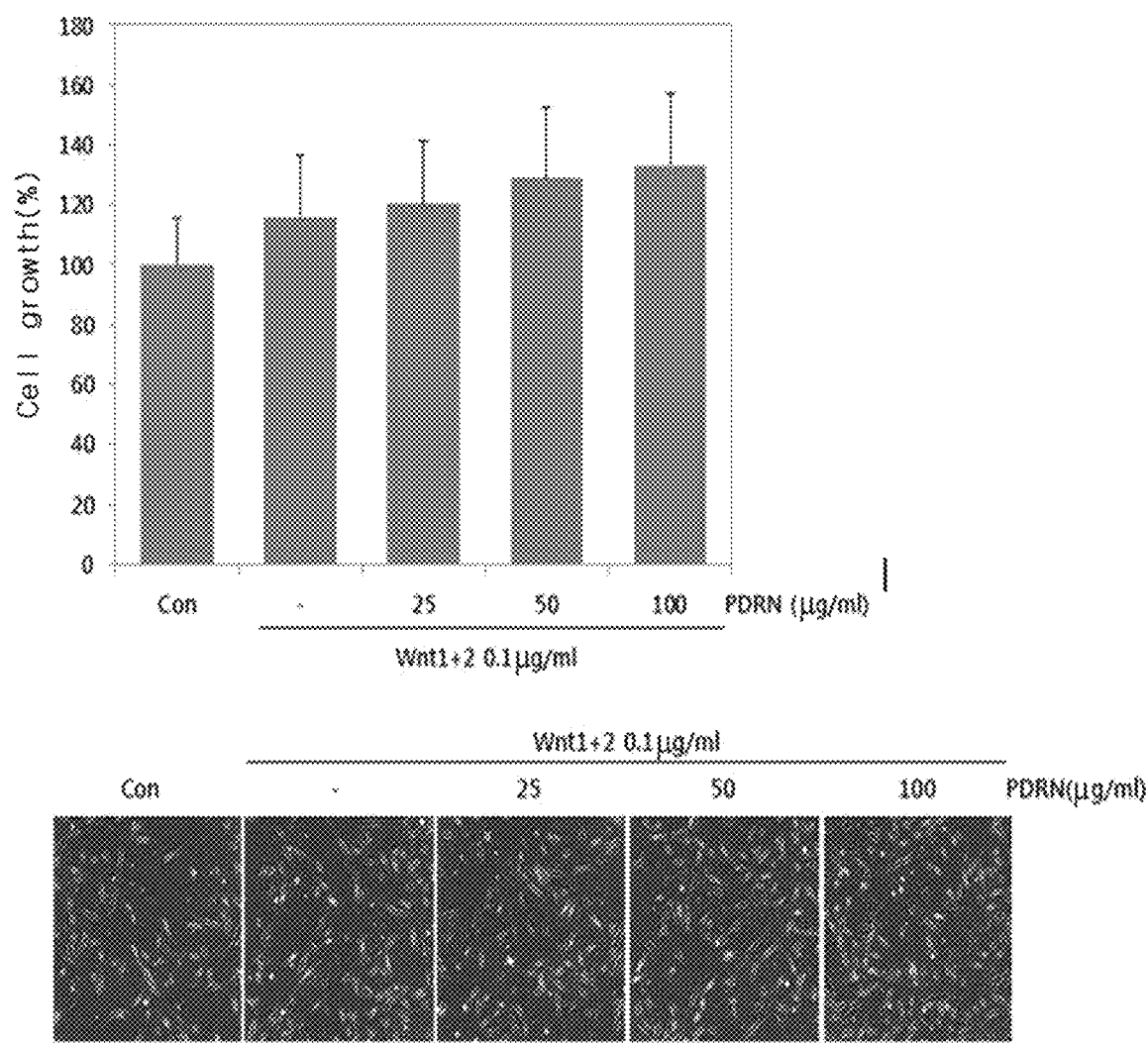
FIG. 5 shows the effect of promoting cell growth by Wnt-1+Wnt-2+PDRN using dermal papilla cells, and microscopic images thereof.

As a result, as shown in FIG. 5, when the treatment was performed in conjunction with PDRN, the growth rate of the cells was increased, and also, as the treatment concentration of PDRN increased, the growth rate of the dermal papilla cells was increased, compared with the Wnt-1+Wnt-2 alone treatment.

Example 5: Expression Analysis of β-Catenin and c-Myc

As in Example 1, the dermal papilla cells were stabilized for at least 4 hours after seeding in 6 well plates at $4\times10^4$ cells/well. Thereafter, the medium was removed, and the cell was treated with PDRN, Wnt-1 peptide and Wnt-2 peptide at various concentrations alone or in combination and incubated for 72 hours in an incubator at 37° C., 5% $CO_2$.

Then, the cells were lysed by adding lysis buffer (1 M Tris-HCl, 0.5 M EDTA, 1% Triton X-100, 100 mM PMSF) to each cell, and the protein was quantified using a BCA (Bicinconinic acid) kit. 20 μg of protein was loaded on 10% SDS-polyacrylamide and electrophoresed at 125 V. The protein separated by electrophoresis was transferred to PVDF membrane (Immobilon-P transfermembrane) by electrophoresis at 50 mA for 120 minutes using transfer buffer (20% methanol, 25 mM Tris-HCl, 192 mM glycine).

To prevent nonspecific binding, the membranes were blocked with 5% non-fat skim milk and then the reaction was carried out at 4° C. for 12 hours with a primary antibody (β-catenin, c-myc, Santa Cruz Biotechnology, Inc.) diluted to 1:1000 in TTBS solution (137 mM Tris-CI, pH 7.4; 20 mM NaCl; 0.05% Tween-20). Thereafter, the membrane was washed three times with TTBS and reacted with a secondary antibody (HRP-conjugated anti-rabbit IgG) diluted to 1:2000 at room temperature for 2 hours. The membrane was then washed three times with TTBS and then protein expression was confirmed on the X-ray film using an ECL diagnostic kit.

Figure 6:
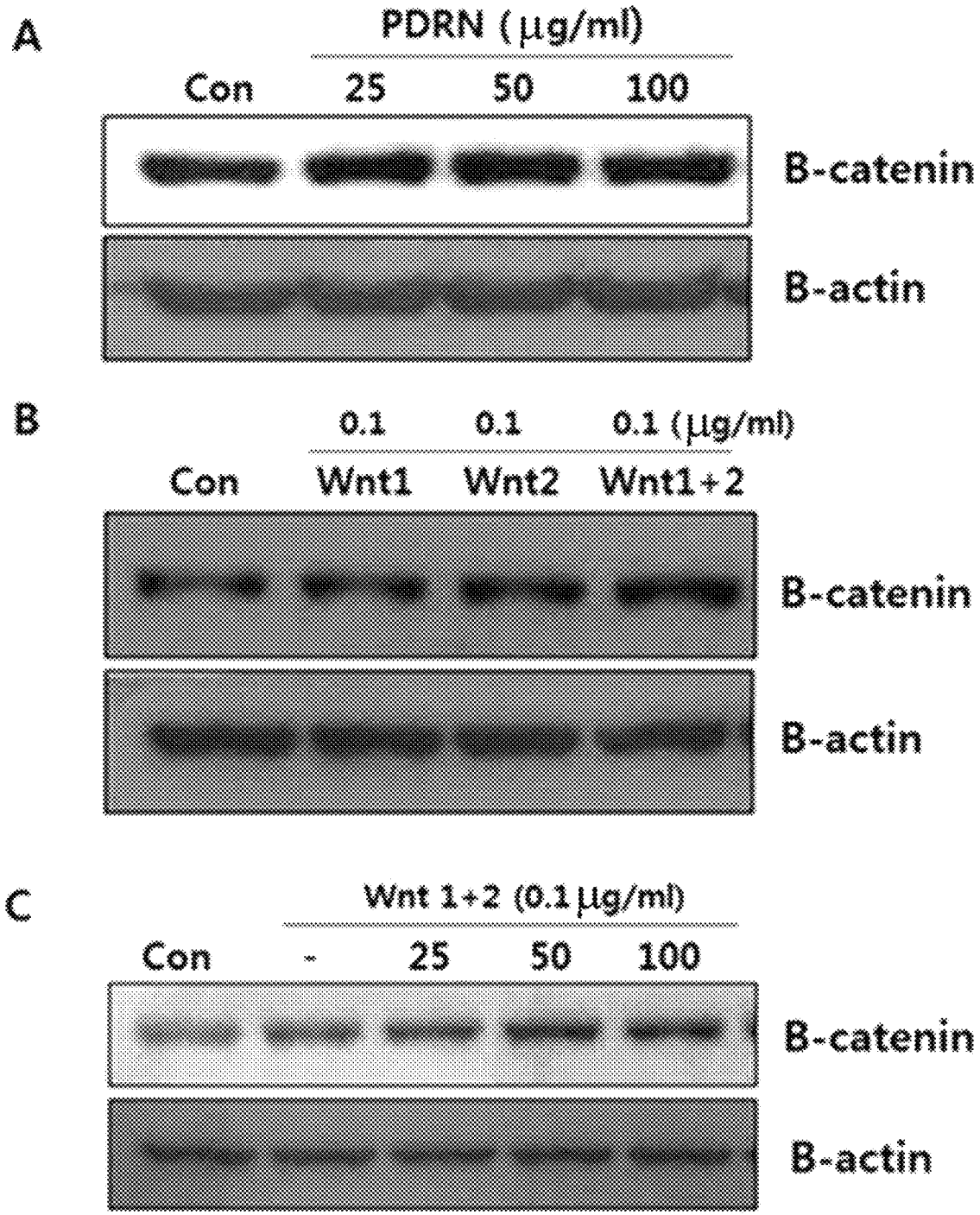
FIG. 6 shows the effect of increasing the activity of β-catenin by (A) PDRN, (B) Wnt-1, Wnt-2, Wnt-1 and Wnt-2, (C) Wnt-1 and Wnt-2 using dermal papilla cells.

As a result, as shown in FIG. 6, when the treatment was performed in combination of Wnt-1+Wnt-2, the expression of β-catenin increased compared with the Wnt-1 or Wnt-2 alone treatment, and when the PDRN additionally treated, it was confirmed that the expression of β-catenin increased in concentration-dependent manner.

Figure 7:
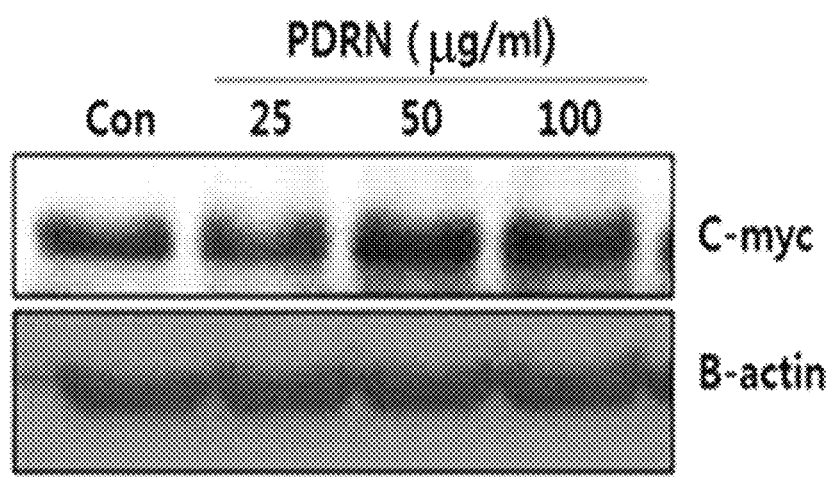
FIG. 7 shows the effect of increasing the activity of c-myc by (A) PDRN, B) Wnt-1, Wnt-2, Wnt-1+Wnt-2, Wnt-1+ PDRN, Wnt-2+PDRN, Wnt-1+Wnt-2+PDRN using dermal papilla cells.
Figure 7:
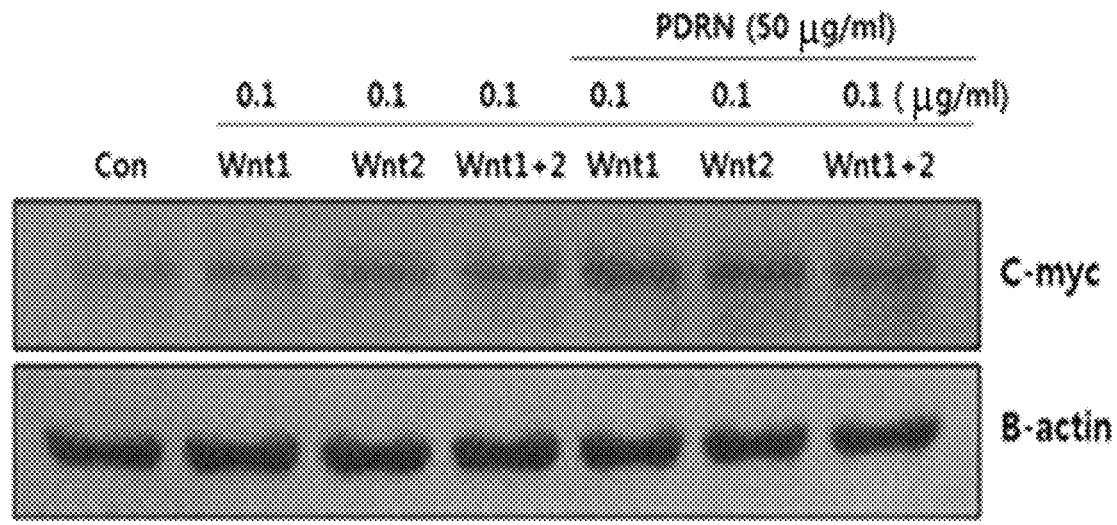

In addition, as shown in FIG. 7, the expression of c-myc increased as the treatment concentration of PDRN increased, and when Wnt was treated in conjunction with PDRN, it was confirmed that the expression of c-myc increased.

Example 6: Analysis of the Effect of Promoting Hair Growth on Treatment of Wnt Peptide in Conjunction with PDRN in C57BL/6 Mice In order to analyze the effect of promoting hair growth by treatment of Wnt peptide (Wnt-1+Wnt-2) in conjunction with PDRN, in vivo hair growth experiments were performed using C57BL/6 mice, which are most used for hair growth testing.

Seven-week-old female C57BL/6 mice (Orient Bio Co., Ltd.) with similar weight to each other were subjected to experiments at the age of 8 weeks after acclimatization for 1 week at 25° C. and 50% humidity. The mouse was placed in a desiccator containing ether, anesthetized for 1 minute, and the hair on the back of the mouse was removed with a hair removal cream. Wnt peptide (Wnt-1+Wnt-2, 5 µg/mL or 15 µg/mL) and PDRN (2.5 mg/mL or 7.5 mg/mL) were applied transdermally to the back area from the day of hair removal and 200 µL of the sample was applied once a day. After application for 15 days, photographs were taken to confirm the degree of hair growth by checking the color change of the application site. Minoxidil of 3% was used as a positive control and phosphate buffer was used as a negative control.

Figure 8:
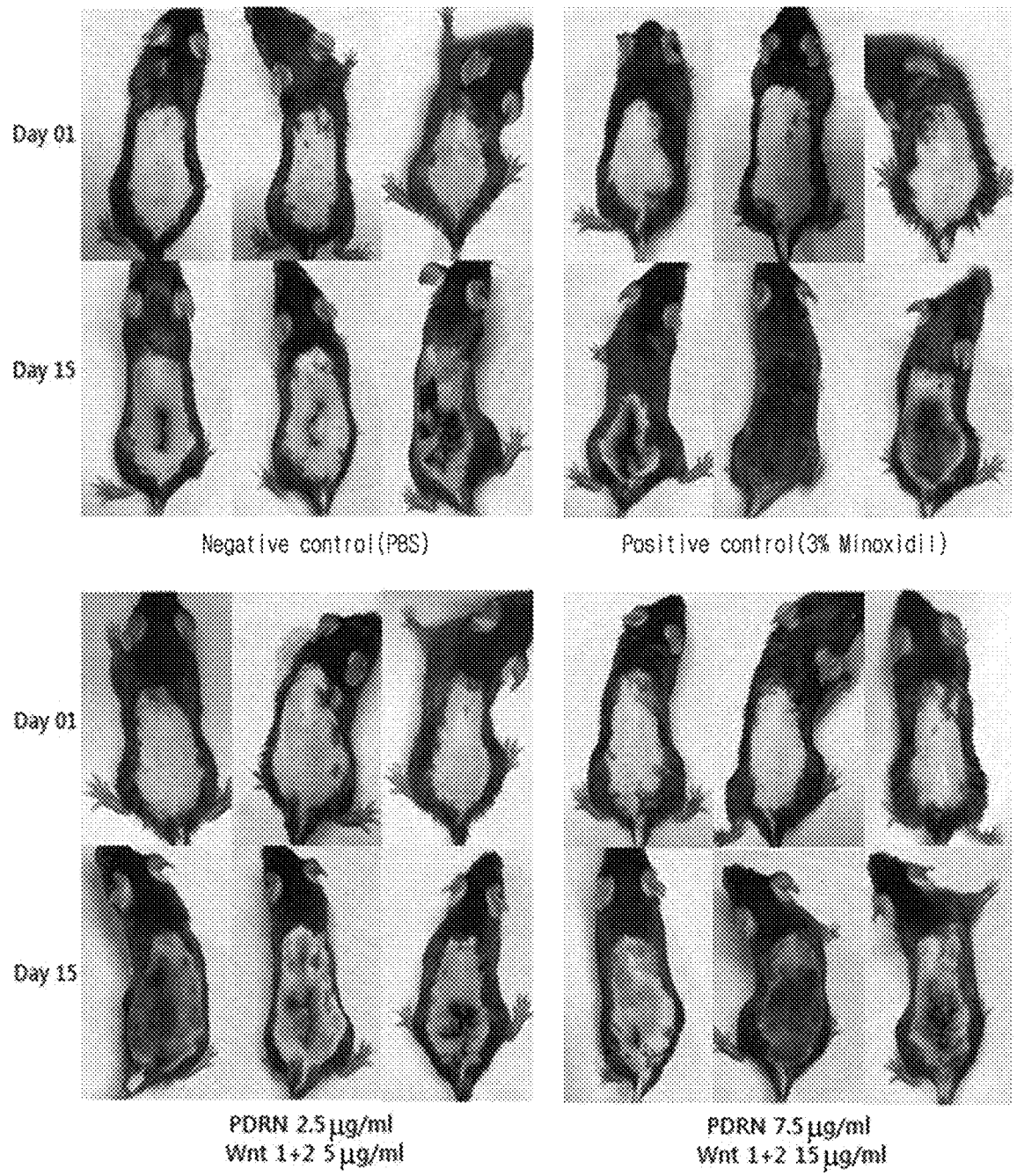
FIG. 8 shows the hair growth effect by Wnt-1+Wnt-2+ PDNR using the hair-removed C57BL/6 mice.

As a result, as shown in FIG. 8, the group having the treatment of Wnt peptide (Wnt-1+Wnt-2) in conjunction with PDRN dramatically increased the hair growth compared with the negative control group and exhibited the hair growth effect similar to the positive control level.

According to the present invention, Wnt protein-derived peptides, polydeoxyribonucleotides or mixtures thereof increase the secretion of β-catenin, and increase the growth of keratinocytes, fibroblasts and dermal papilla cells which are hair constituent cells, by the cell activation and activation of signal transduction pathway for promoting the hair growth signaling system and to prevent the hair loss and promote the hair growth and therefore, Wnt protein-derived peptides, polydeoxyribonucleotides or mixtures thereof having the above effect can be used as a cosmetic composition, a pharmaceutical composition or a health food composition for preventing the hair loss or promoting the hair growth.

As described above in detail specific parts of the present invention, it is apparent to those skilled in the art that these specific descriptions are merely preferred embodiments, and the scope of the present invention is not limited thereto. Accordingly, the substantial scope of the present invention will be defined by the appended claims and equivalents thereof.

The scope of the present invention is represented by the following claims, and it should be construed that all changes or modifications derived from the meaning and scope of the claims and their equivalents are included in the scope of the present invention.

What is claimed is:

1. A method of promoting hair growth in a subject, comprising:
   providing a cosmetic composition comprising a peptide comprising SEQ ID NO: 1 and SEQ ID NO: 2, and polydeoxyribonucleotide, as an active ingredient; and
   administering the cosmetic composition to the subject, wherein the hair growth is promoted.

2. The method of claim 1, wherein the peptide is acetylated at N-terminus of the amino acid sequence.

3. The method of claim 1, wherein the peptide is a peptide derived from Wnt protein.

4. The method of claim 1, wherein the polydeoxyribonucleotide is separated from fish testis.

5. The method of claim 4, wherein the fish is selected from the group consisting of salmon, trout, herring, pollock and cod.

6. The method of claim 1, wherein the polydeoxyribonucleotide has a number average molecular weight of 350 to 2000 kDa.

7. The method of claim 1, wherein the composition promotes growth of keratinocytes, fibroblasts and dermal papilla cells by increasing secretion of β-catenin.

8. The method of claim 1, wherein the composition increases c-myc expression.

9. The method of claim 1, wherein the composition is formulated in a formulation selected from the group consisting of hair tonic, hair conditioner, hair essence, hair lotion, hair nutrition lotion, hair shampoo, hair rinse, hair treatment, hair cream, hair nourishing cream, hair moisturizer cream, hair massage cream, hair wax, hair aerosol, hair pack, hair nutrition pack, hair soap, hair cleansing foam, hair oil, hair drying agent, hair preservative, hair dye, hair wave agent, hair bleach, hair gel, hair glaze, hair dressinger, hair lacquer, hair moisturizer, hair mousse and hair spray.

* * * * *

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide derived from Wnt-1 protein

<400> SEQUENCE: 1

Met Cys Cys Gly Arg Gly Tyr Asp Gln Phe
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide derived from Wnt-2 protein

<400> SEQUENCE: 2

Met Cys Cys Gly Arg Gly Tyr Asn Tyr His
1               5                   10
```